(12) United States Patent
Powers

(10) Patent No.: US 8,394,062 B2
(45) Date of Patent: Mar. 12, 2013

(54) FLOATING GEARBOX APPARATUS AND METHOD

(75) Inventor: Benjamin G. Powers, Portsmouth, NH (US)

(73) Assignee: Fluidnet Corporation, Amesbury, MA (US)

( * ) Notice: Subject to any disclaimer, the term of this patent is extended or adjusted under 35 U.S.C. 154(b) by 171 days.

(21) Appl. No.: 13/084,062

(22) Filed: Apr. 11, 2011

(65) Prior Publication Data

US 2011/0251557 A1    Oct. 13, 2011

Related U.S. Application Data

(60) Provisional application No. 61/323,168, filed on Apr. 12, 2010.

(51) Int. Cl.
  *A61M 1/00* (2006.01)

(52) U.S. Cl. ........ 604/151; 74/425; 74/606 R; 74/421 A

(58) Field of Classification Search ................... 604/151, 604/131; 74/425, 421 A, 606 R
See application file for complete search history.

*Primary Examiner* — Laura Bouchelle
(74) *Attorney, Agent, or Firm* — Chapin IP Law, LLC

(57) ABSTRACT

A floating gearbox includes an outer housing with first and second side walls opposite and spaced apart from each other and an inner gear assembly received within the outer housing. The inner gear assembly comprises an inner housing, a first gear member rotatably received within the inner housing, and a second gear member having an output shaft rotatably supported on the inner housing. A slider plate received within the outer housing has first and second pairs of axially aligned elongate openings, wherein the first and second pairs of elongate openings align with a first axis and a second axis, respectively. Pins on the first sidewall are received in the first pair of elongate openings to allow relative sliding movement between the outer housing and the slider plate along the first axis. The inner housing includes pins received in the second pair of elongate openings, allowing relative sliding movement between the inner housing and the slider plate along the second axis.

13 Claims, 9 Drawing Sheets

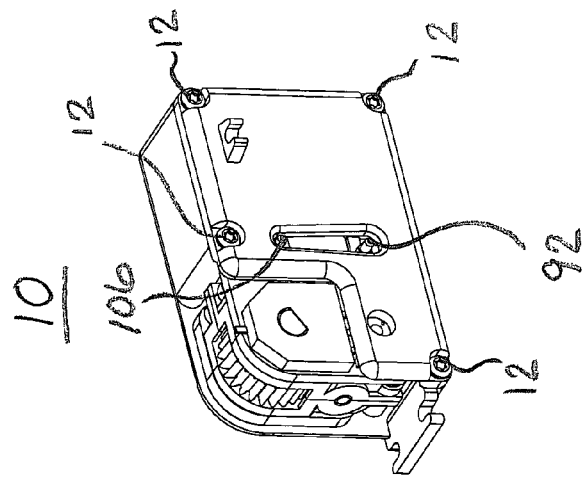
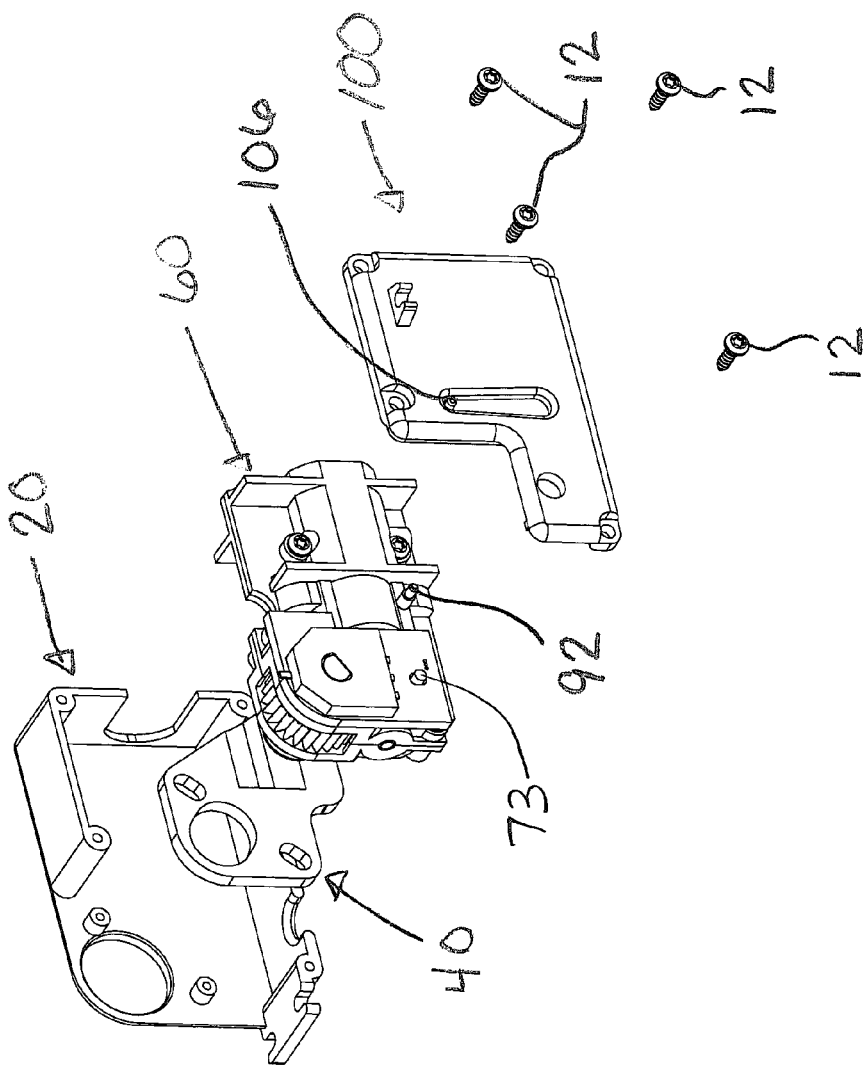

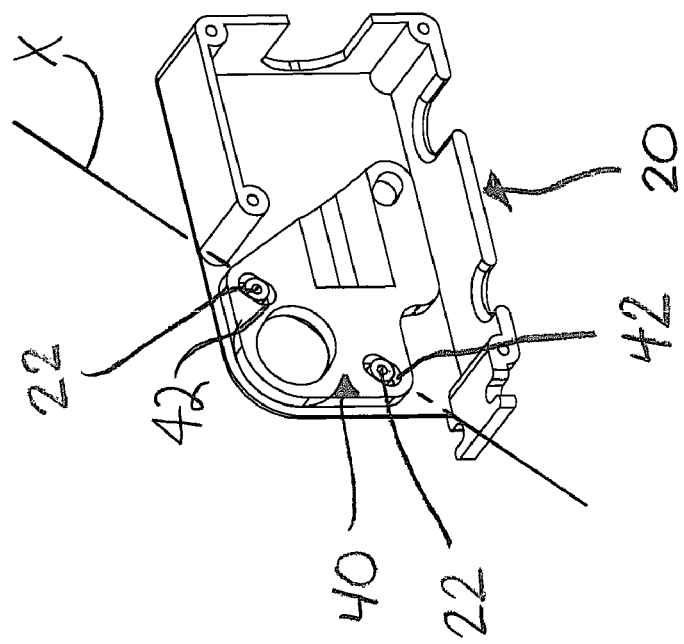
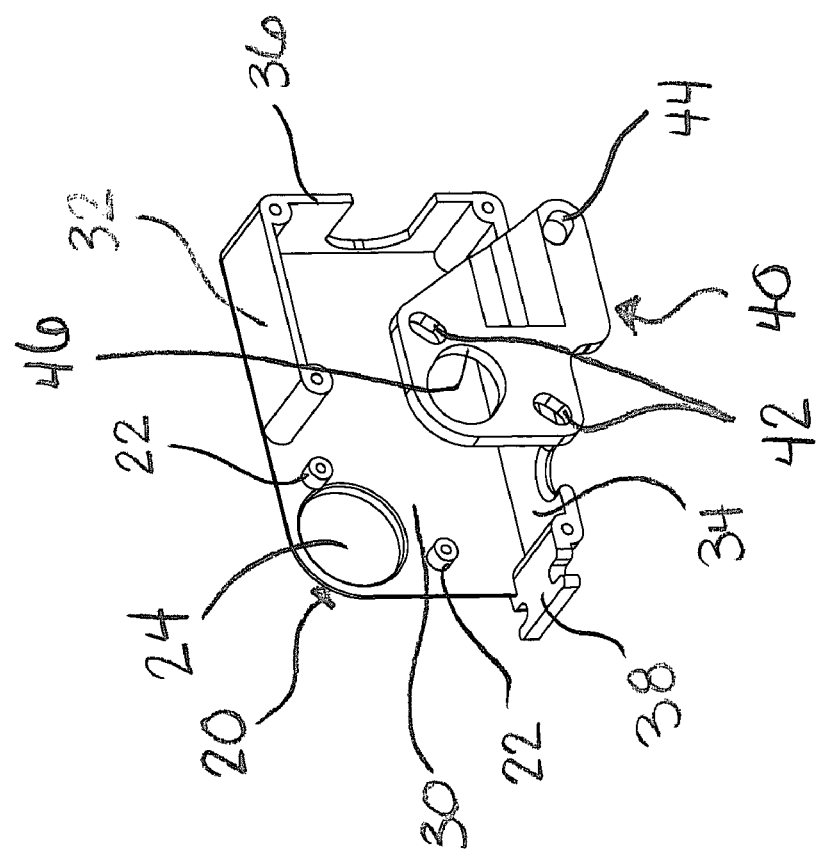

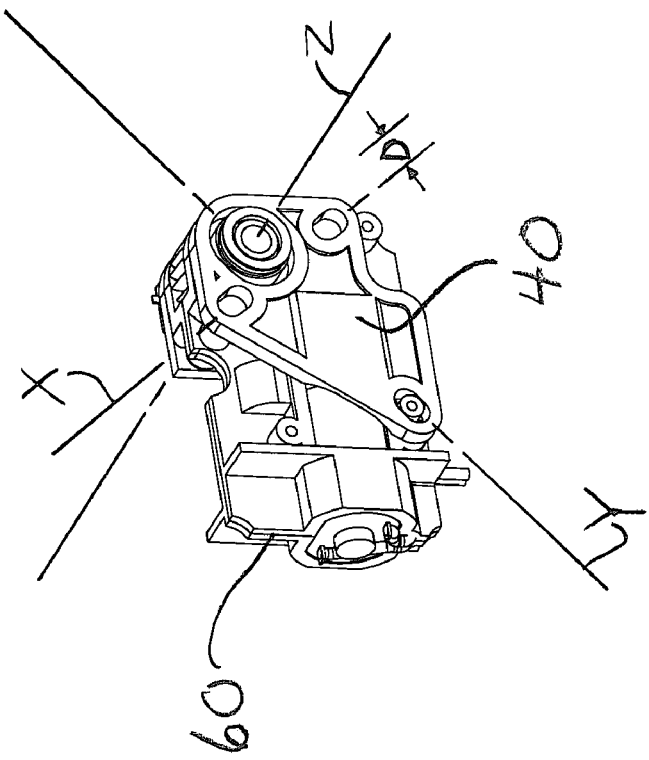
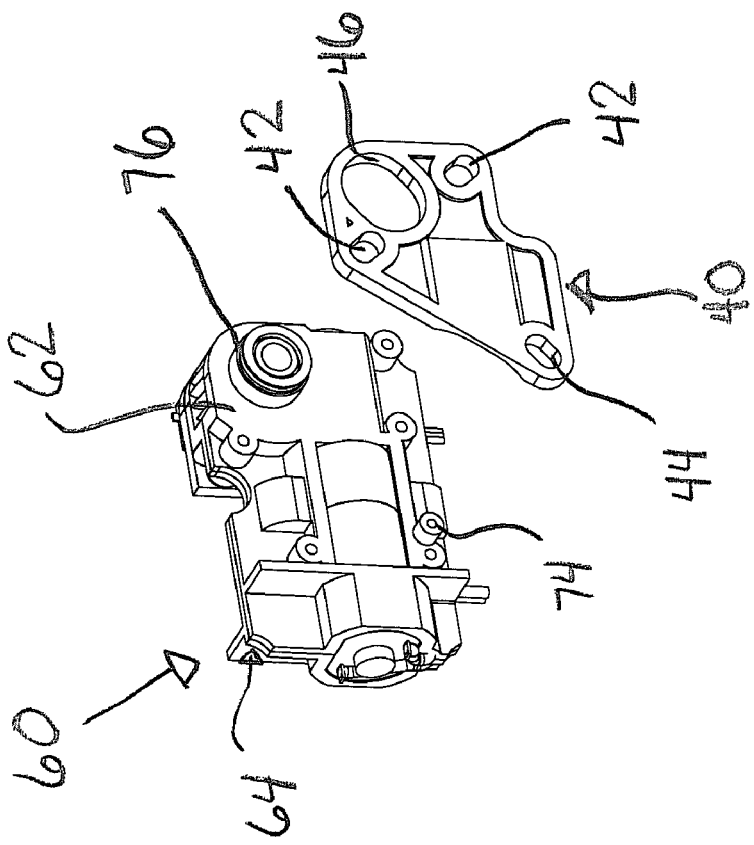

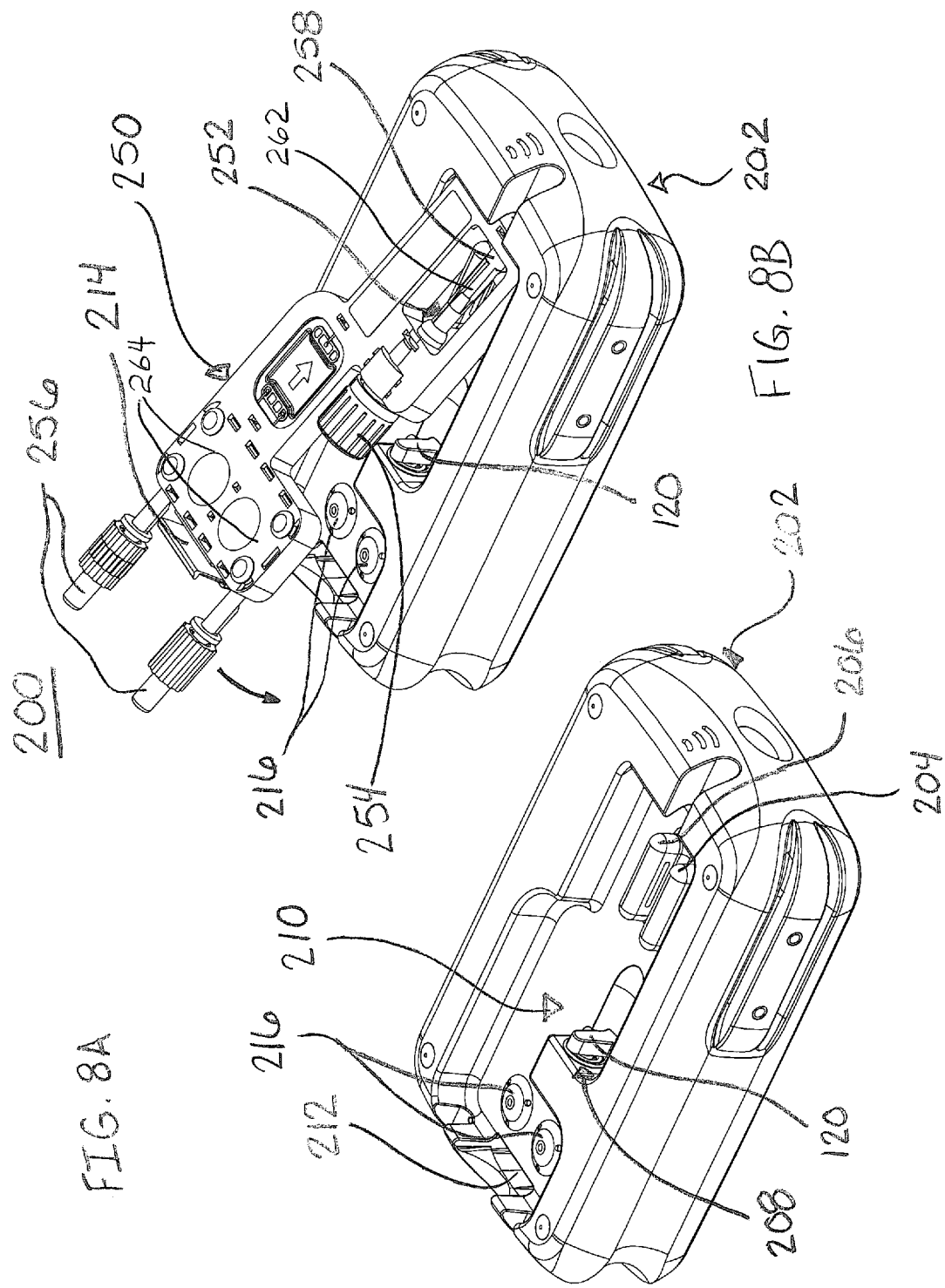

FLOATING GEARBOX APPARATUS AND METHOD

CROSS-REFERENCE TO RELATED APPLICATION

This application claims the priority benefit under 35 U.S.C. §119(e) of U.S. provisional patent application Nos. 61/323,168 filed Apr. 12, 2010, which is incorporated herein by reference in its entirety.

BACKGROUND

The present disclosure relates to a floating gearbox apparatus and method. The present development will be described primarily by way of reference to a gearbox for use in a fluid flow control system such as an intravenous (IV) pump. However, it will be recognized that the present gearbox will find utility in all manner of applications wherein it is desired to couple the output shaft of a gear transmission system to a shaft to be driven.

Flexible couplings for joining drive shafts exist; however, they only accommodate slight axial and angular misalignment. It would, therefore, be desirable to provide a gear transmission system that can accommodate a large tolerance loop between the location of the output shaft and the location of the driven shaft.

Additionally, the standard flexible couplings are primarily designed to couple two permanently fixed shafts. It would also be desirable to provide a gear transmission system that couples an output shaft to a snap in driven shaft.

One disadvantage of flexible shaft couplings is that they induce a torsional flexibility into the system, which can result in an error if the position of the driven shaft is being read by an encoder. It would, therefore, also be desirable to provide a gear transmission system that does not induce torsional flexibility into the system.

Accordingly, the present disclosure contemplates a floating gearbox that overcomes the above problems and others. The present disclosure also contemplates a fluid control system and method employing the same.

SUMMARY

In one aspect, the present disclosure provides a gearbox for transmitting rotation from an input shaft to an output shaft, wherein the gearbox is movable along two intersecting (and preferably perpendicular) axes lying in a plane that is perpendicular to the axis of rotation of the output shaft. In more limited aspects, a gearbox for adjusting a flow resistor in a flow control system, and a method and flow control system employing the same, are provided. The floating gearbox disclosed herein includes an outer housing, a slider plate, and an inner gearbox assembly. The outer housing comprises a front housing component and a rear housing component. The slider plate comprises a plate having two elongated openings along a first axis and two elongated openings along a second axis. The inner gearbox assembly comprises a front inner housing component, a rear inner housing component, a motor driving a worm, a helical gear driven by the worm, and a rotary encoder for sensing a rotational position of an output shaft of the helical gear.

The slider plate is placed on the inner gearbox assembly aligning the two pins on the inner gearbox assembly with the corresponding openings on the slider plate, enabling the slider plate to move in a first direction relative to the inner gearbox assembly. The inner gearbox assembly and slider plate combination is then placed into the front outer housing component aligning the two pins on the front outer housing component with the corresponding openings on the slider plate, enabling the slider plate to move in a second direction relative to the front outer housing.

In exemplary embodiments, the two sets of openings in the slider plate are perpendicular, enabling the inner gearbox assembly to move in two cardinal directions, without causing any coupling or restorative forces when a torque is applied at the output shaft, which extends in the third cardinal direction. In further embodiments, the drive axis may be in line with two axes of movement of the slider plate. However, as shown in the depicted embodiment, the slider plate elongate openings may be offset relative to the drive axis, for example, where space of size limitations of the gearbox dictate, although it is desirable in such instances that the slider plate openings be placed as close as possible to the output axis to reduce any off-axis forces at the output shaft.

Once the inner gearbox assembly and slider plate have been properly aligned and placed within the front outer housing component, the rear outer housing component is placed over the inner gearbox assembly and slider plate combination and secured via mechanical fasteners. After the floating gearbox is secured, an output drive shaft is inserted into the gear shaft and a tension member is then connected between a spring pin on the rear outer housing and a spring pin on the inner gearbox assembly. The tension member preloads the gearbox into the upper, centered position. The tension member should provide only a relatively small force, i.e., one that is large enough only to ensure that the gearbox is centered, while not imparting any significant force against the driven shaft.

In the depicted preferred embodiment, the floating gearbox is assembled and mounted into a pump assembly. The front and rear outer housing shells of the floating gearbox are rigidly attached to bosses inside the pump housing. When the pump assembly is ready to be used, an administration set is snapped into the pump assembly and the output drive shaft of the floating gearbox assembly is pushed into the correct position to drive the adjustment cap (i.e., the driven shaft) of the fluid flow resistor. When assembled, the slider plate enables the output shaft of the floating gearbox to float freely as it interfaces with the adjustment cap, thereby reducing or minimizing the potential for binding.

In another aspect, a method for controlling a fluid flow rate in a flow control system using a floating gearbox assembly is provided. Infusion data is input and processing electronics operate the motor under programmed control to rotate the output drive shaft via the floating gear transmission system. The output drive shaft, in turn, drives an adjustment cap of the fluid flow resistor to vary the valve position in a fluid flow resistor to thereby control or adjust the rate of fluid flow to the patient.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention.

FIG. 1A is a partially exploded isometric view of an exemplary floating gearbox embodiment.

FIG. 1B is an isometric view of the exemplary floating gearbox embodiment appearing in FIG. 1A.

FIG. 2A is an exploded side view of the front outer housing and slider plate of the floating gearbox.

FIG. 2B is an isometric view of the front outer housing and slider plate of the floating gearbox shown in FIG. 2A.

FIG. 3A is an exploded isometric view of the inner gearbox assembly and slider plate of the floating gearbox.

FIG. 3B is an isometric view of the inner gearbox assembly and slider plate of the floating gearbox shown in FIG. 3A.

FIG. 8A is an isometric view of the pump assembly with the floating gearbox mounted into the pump assembly, taken generally from the front and side.

FIG. 8B is an isometric view of the pump assembly appearing in FIG. 8A, with an administration set partially snapped into the pump assembly.

DETAILED DESCRIPTION OF THE PREFERRED EMBODIMENTS

Figure 4:
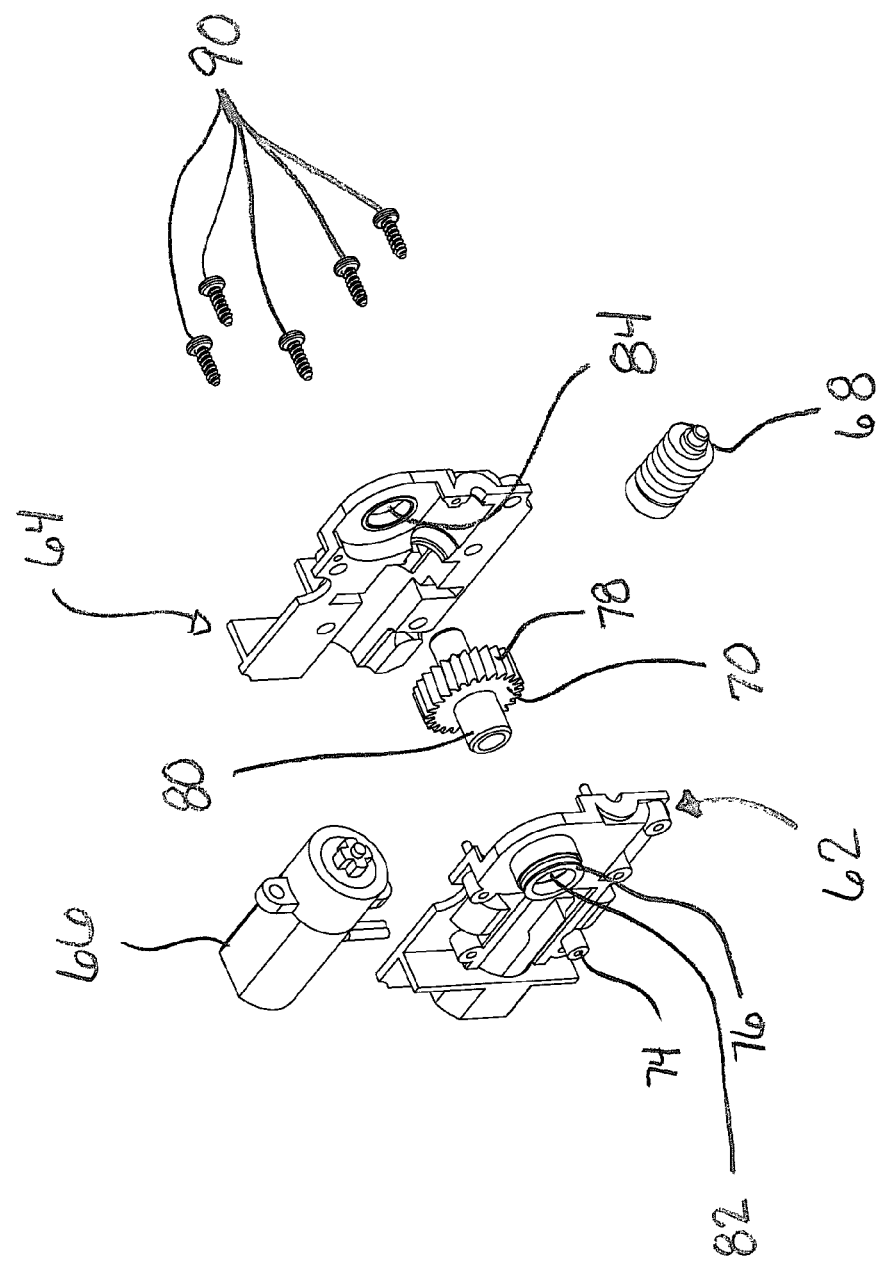
FIG. 4 is an exploded view of the inner gearbox assembly.

Referring to the drawings, wherein like reference numerals are used to indicate like or analogous components throughout the several views, and with particular reference to FIGS. 1A and 1B, there is illustrated an exemplary embodiment floating gearbox 10, which includes a front outer housing 20, a slider plate 40, an inner gearbox assembly 60, and a rear outer housing 100. The slider plate 40 and inner gearbox assembly 60 are secured between the front outer housing 20 and rear outer housing 100. The front housing 20 is secured to the rear housing 100 via mechanical fasteners 12, such as screws, rivets, clips, dogs, pawls, or the like.

As best seen in FIGS. 2A and 2B, the front outer housing 20 contains a front wall 30, a first side wall 32, a second side wall 34, and a third side wall 36. The front wall 30 has an opening 24 and pins 22 on its interior surface. The slider plate 40 contains elongated openings 42, which align with and slidably receive the respective aligned pins 22 of the front housing 20. The long axis of the openings 42 are aligned with the X axis to allow relative sliding movement between the front outer housing shell 20 and the slider plate 40 in the X axial direction.

The slider plate 40 also contains an elongated opening 44 and a large, elongated opening 46. The large opening 46 aligns with opening 24 of the front housing 20 when the slider plate 40 and the inner gearbox assembly 60 are secured within the front and rear housings, 20 and 100 respectively.

Referring now to FIGS. 3A and 3B, the inner gearbox assembly 60 includes a front inner gearbox assembly housing 62 and a rear inner gearbox assembly housing 64. The front inner gearbox assembly housing 62 contains pins 74 and 76. The pin 74 is slidably received within the elongated opening 44 and the pin 76 is slidably received within the opening 46 when the slider plate 40 is placed on the inner gearbox assembly 60. The long axis of the openings 44 and 46 are aligned with the Y axis to allow relative sliding movement between the inner gearbox assembly 60 and the slider plate 40 in the Y axial direction. In the depicted embodiment, the X and Y axes are perpendicular to each other and each is perpendicular to the axis of rotation of the output shaft 80, which is designated the Z axis.

In the depicted embodiment, the Y axis intersects with the Z axis, which minimizes or reduces the potential for binding by eliminating off-axis forces. In the depicted embodiment, by using one of the pins 74 or 76 (76 in the depicted embodiment) as the bearing surface for the helical gear 70, it is ensured that the output axis Z is aligned with the Y axis of the sliding openings 44 and 46. It will be recognized, however, space or configuration requirements may require that one of the X or Y axes be displaced or offset from the Z axis, in which case, such offset axis should be placed as close as possible to the Z axis to minimize off-axis forces. For example, in the depicted embodiment, the X axis intersects the Y axis at an offset distance D from the Z axis, as described below.

Figure 5:
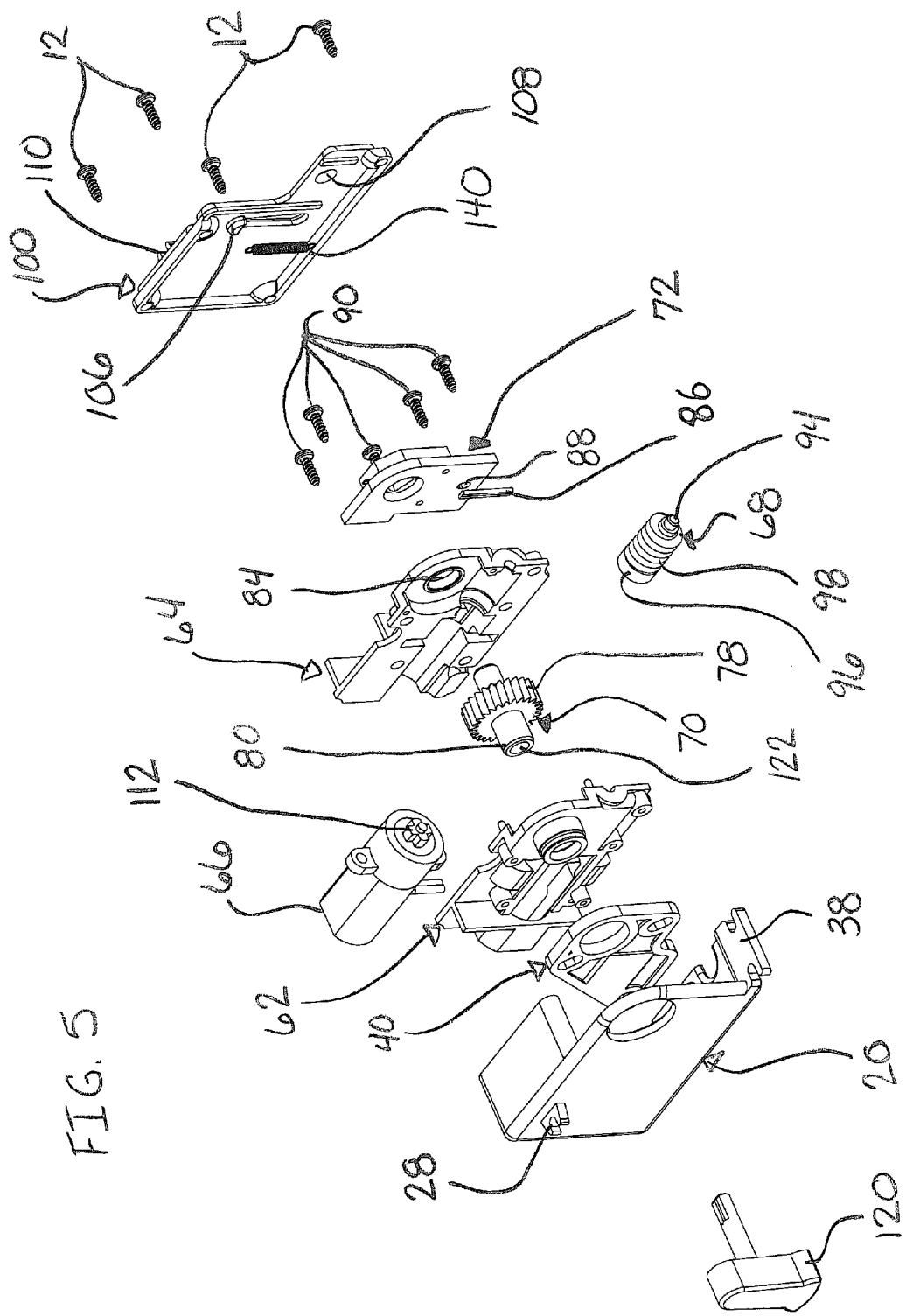
FIG. 5 is an exploded view of the floating gearbox.

As best seen in FIGS. 4 and 5, the inner gearbox assembly 60 further includes a motor 66, such as a DC gearmotor, which drives a worm 68. The worm 68, in turn, drives a helical gear or worm wheel 70. An encoder board 72 including a rotary encoder senses the rotational position of the output shaft 80 of the helical gear 70.

The worm 68 has a first end 94, a second end 96, and at least one helical tooth 98. The helical tooth 98 starts at the first end 94 and travels partially down the worm 68 toward the second end 96 in a helical or thread-like fashion. The helical gear 70 has a plurality of teeth 78 and a gear shaft 80 with an opening 122. The motor shaft 112 of the motor 66 mates with the second end 96 of the worm 68 and the helical tooth 98 of the worm 68 mates with the teeth 78 of the helical gear 70. The teeth 78 may be inclined or angled to intermesh with the thread 98 of the worm 68.

The motor 66, worm 68, and helical gear 70 are contained and supported within the inner housing shell defined by the front inner gearbox assembly housing 62 and the rear inner gearbox assembly housing 64 via mechanical fasteners 90. The gear shaft 80 of the helical gear 70 interacts with the exterior environment via a first opening 82 on the front inner housing 62 and a second opening 84 on the rear inner housing 64.

The encoder board 72 is secured to the exterior of the rear inner gearbox assembly housing 64. The encoder board 72 of the inner gearbox assembly 60 has an opening 88, which aligns with an alignment pin 73 on the rear inner housing shell 64 to ensure proper alignment of the rotary encoder 72. A clearance opening 108 is also formed in the rear outer housing 100 to provide a clearance for the pin 73.

Referring now to FIGS. 6A, 6B, 7A, and 7B and with continued reference to FIGS. 1-5, the slider plate 40 is placed on the inner gearbox assembly 60, with the pins 74 and 76 on the inner gearbox assembly 60 slidably received within the corresponding openings 44 and 46 on the slider plate 40. The openings 44 and 46 enable the slider plate 40 to move in the Y axial direction relative to the inner gearbox assembly 60.

The inner gearbox assembly 60 and slider plate 40 combination is then placed into the front outer housing 20, with the pins 22 on the front outer housing 20 slidably received within the corresponding aligned openings 42 on the slider plate 40. The openings 42 enable the slider plate 40 to move in the X axial direction relative to the front outer housing 20.

In the exemplary illustrated embodiment, the X and Y axes are perpendicular to each other, enabling the inner gearbox assembly 60 to float in two cardinal directions without causing any coupling or restorative forces when a torque is applied at the output shaft 120. In certain embodiments, the X axis defined by the long axes of the openings 42 may be aligned with the Z axis (output drive axis) to reduce or minimize any off axis forces and is preferable where space permits. In the depicted embodiment, however, the X axis is shown slightly offset by an offset distance D with respect to the Z axis, as may be necessary depending on the space constraints of a given application. In such cases, the X axis defined by the openings 42 should be placed as close to the Z output axis as possible to reduce or minimize off-axis forces.

Figure 6B:
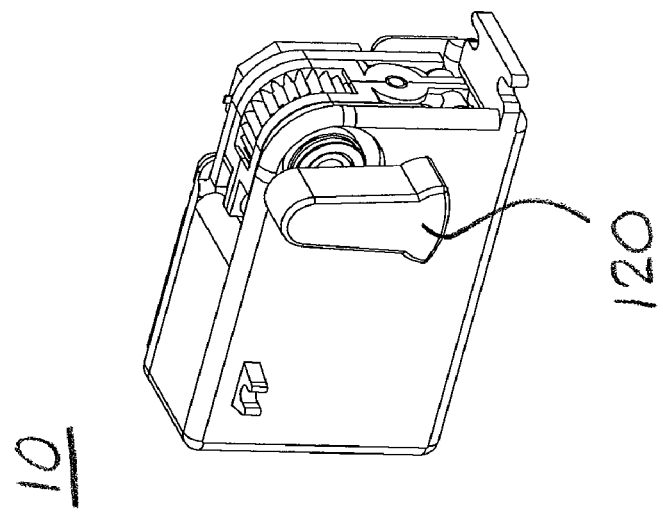
FIG. 6B is an isometric view of the floating gearbox with the output drive shaft attached.
Figure 6A:
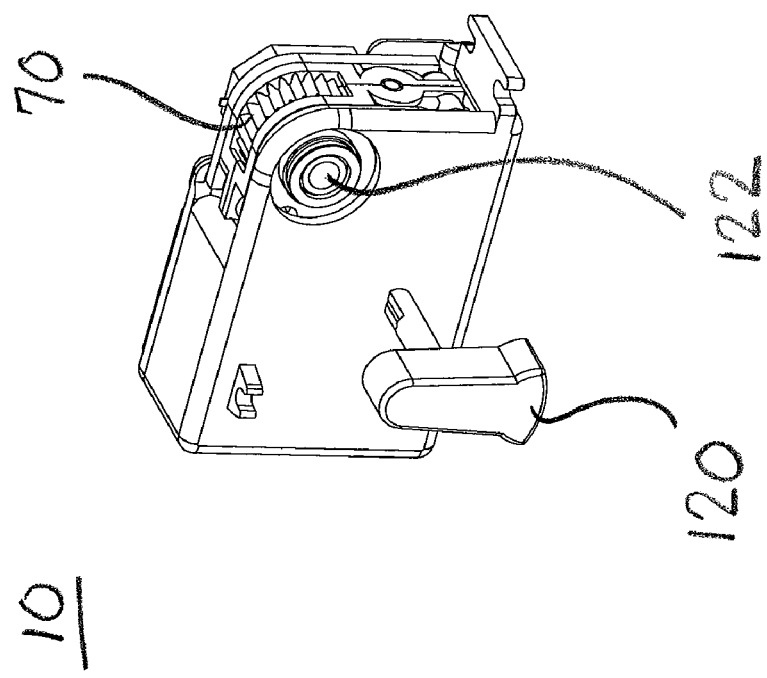
FIG. 6A is a partially exploded view of the floating gearbox illustrating the means of attachment of the output drive shaft to the floating gearbox.

Once the inner gearbox assembly 60 and slider plate 40 have been properly aligned and placed within the front outer housing 20, the rear outer housing 100 is placed over the combination of the inner gearbox assembly 60 and slider plate 40 and secured via mechanical fasteners 12. An output drive shaft 120 is inserted into the gear shaft 80 via the opening 122, as best seen in FIGS. 6A and 6B.

Figure 7A:
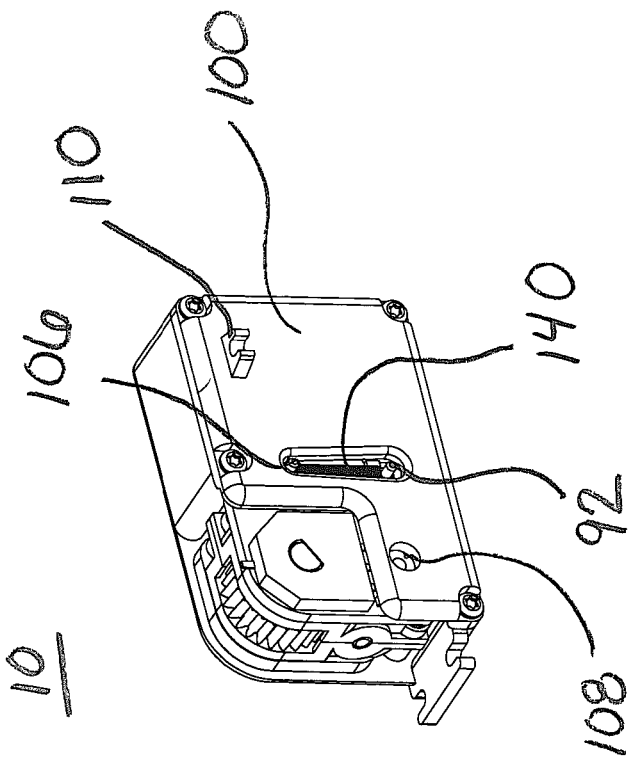
FIG. 7A is a partially exploded view of the floating gearbox illustrating the means of attachment of the biasing spring to the floating gearbox.
Figure 7B:
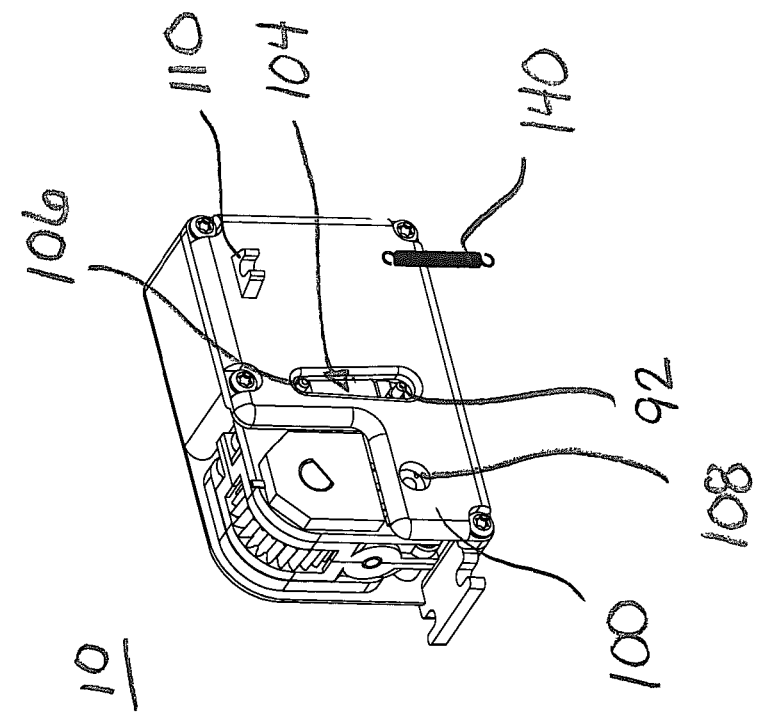
FIG. 7B is an isometric view of the floating gearbox with the biasing spring attached.

As best seen in FIGS. 7A and 7B, a tension member 140 such as a coil spring or the like is connected between a spring pin 106 on the rear outer housing 100 and a spring pin 92 on the inner gearbox assembly 60. The tension member 140 preloads the gearbox 10 into the upper, centered position. The tension member 140 should provide a force that is sufficient to ensure the gearbox 10 is centered, but not so great as to impart a significant force against the shaft to be driven by the output shaft, such as an adjustment cap 254 of an IV administration set 250 (see FIGS. 8A, 8B, and 9) as described below.

Figure 9:
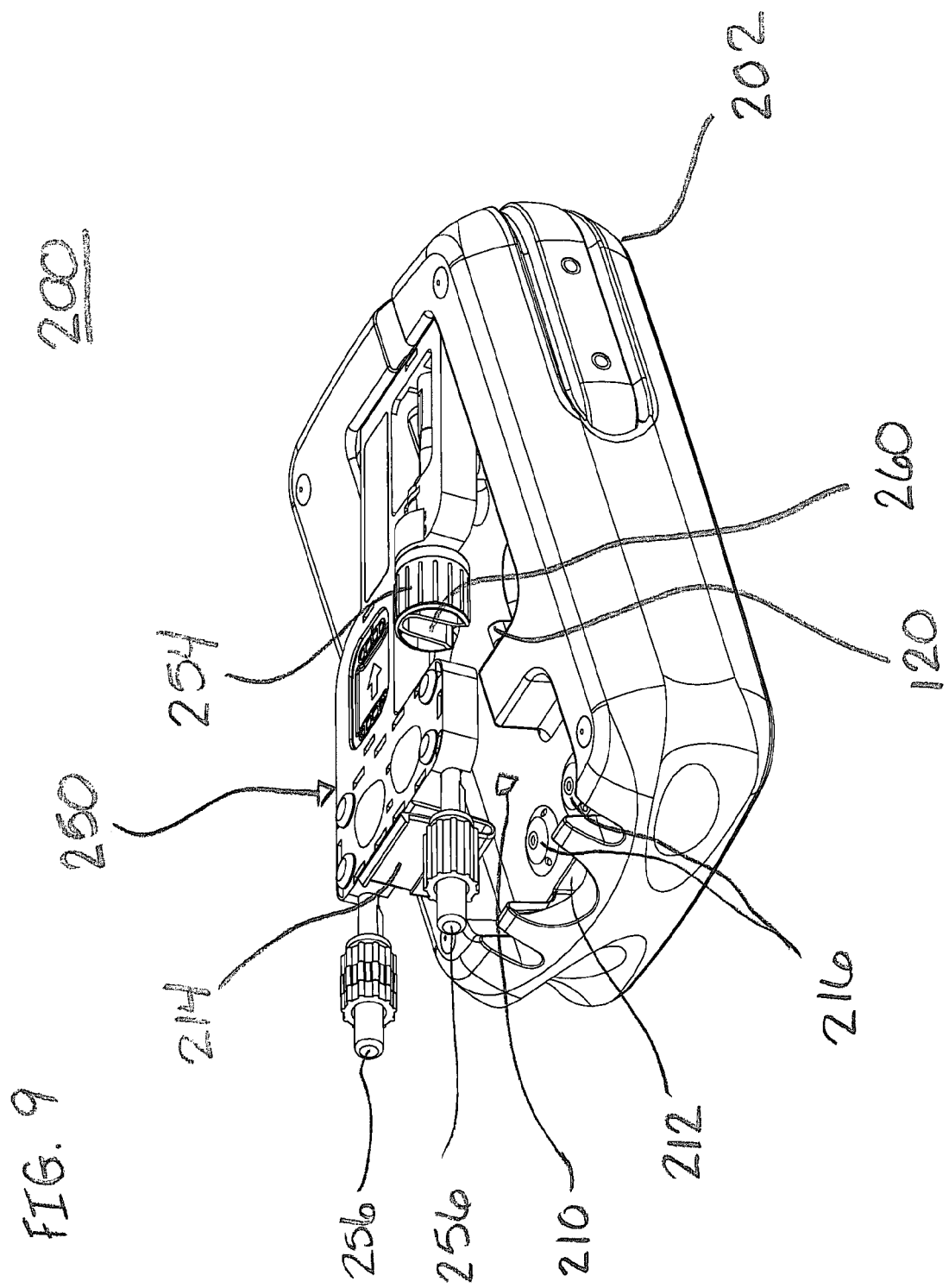
FIG. 9 is an isometric view of the pump assembly appearing in FIG. 8B, taken generally from the rear and side.

Referring now to FIGS. 8A, 8B, and 9, the assembled floating gearbox 10 is mounted in a pump assembly 200 by rigidly attaching the front and rear outer housings 20 and 100, respectively, to the inside of the pump housing 202. In the depicted embodiment, the floating gearbox 10 is secured within the pump housing 202 via a mounting foot 38 and two snap members 28 and 110 (see, e.g., FIG. 5). The pump assembly may be as described in U.S. application Ser. No. 12/906,077 filed Oct. 16, 2010, the entire contents of which are incorporated herein by reference.

The mounting foot 38 of the front outer housing 20 engages the interior of the pump housing 202 and a snap member 28 of the front outer housing 20 is attached to a first boss (not shown) on the interior of the pump housing 202. A snap member 110 of the rear outer housing 100 is attached to a second boss (not shown) on the interior of the pump housing 202. Once the gearbox 10 is secured within the pump housing 202, the output drive shaft 120 protrudes through an opening 208 in the pump housing 202, thus enabling the drive shaft 120 to interface with the adjustment cap 254.

When the pump assembly 200 is ready to be used, an administration set 250 is removably attached into a channel 210 of the pump housing 202. A latch 214 of the administration set 250 is snapped into a groove 212 of the pump housing 202 and a keyed portion of the output drive shaft 120 is pushed into a complimentary groove or receptacle 260 of the adjustment cap 254 in the correct position to drive the adjustment cap 254 of a fluid flow resistor 252.

When assembled, the slider plate 40 enables the output drive shaft 120 of the floating gearbox 10 to float freely in the plane defined by the X and Y axes as it interfaces with the adjustment cap 254, thus minimizing the potential for binding within the gear transmission system due to misalignment between the axis of rotation of the output shaft 120 (the Z axis) and the axis of rotation of the output cap 254 (the driven shaft).

In operation, when the pump assembly 200 is removably secured to the pump housing 202, pneumatic contacts 216 on the pump housing 202 are pneumatically coupled to a corresponding diaphragm of the respectively aligned pumping chambers 264 within the administration set 250. By using a system of manifolds and valves within the pump housing 202 and check valves within the administration set 250, positive or negative air pressure can be selectively applied to the diaphragm of one or both of the pumping chambers 264 in the administration set 250 to selectively pump fluid from fluid sources coupled to fluid inlets 256 through the flow resistor and to the vasculature of a patient.

In operation, instructions are provided by a controller such as a processor, microcontroller, or like processing electronics, to operate the motor 66 and drive the worm 68. As the worm 68 turns, the helical tooth 98 engages the teeth 78 of the helical gear 70, causing the helical gear 70 and the shaft 80 to rotate. The rotation of the helical gear 70, in turn, rotates the output drive shaft 120. When the output drive shaft 120 is interacting with the adjustment cap 254, the rotation of the output drive shaft 120 rotates the adjustment cap 254, which may operate a valve to change the resistance of the fluid flow resistor 252. Because the output drive shaft 120 is able to move or float in the X-Y plane, it is able to accommodate misalignments between the output shaft and the adjustment cap 254. The rotary encoder 72 takes position readings from the output drive shaft 120 to determine the rotational position of the adjustment cap 254. Data readings from the encoder 72 are sent to the processer via a data cable 86.

In an exemplary embodiment, the fluid inlets 256 are fluidically coupled to one or more fluid sources (not shown), as generally known in the art, e.g., an IV infusion fluid, medication, or the like, e.g., via fluid inlet tubes. A fluid outlet 258 may be fluidically coupled to the vasculature of a patient, e.g., via an IV catheter or cannula (not shown), as generally known in the art. Operation of the pump assembly 200 is controlled and monitored by the processor electronics (not shown) within the pump assembly based on input information. For example, an operator, such as a healthcare provider or the patient, can manually input the desired infusion information via a user input interface, such as a keypad, touch screen, or the like (not shown). Alternatively, the infusion information may be input using an alternative input means, such as a bar code reader, RFID tag, or the like.

After the infusion data is input, it is desirable to confirm the infusion data before the infusion can begin. Once the infusion information is input and confirmed, the processing electronics will determine the proper setting for the fluid flow resistor 252. The flow resistor setting may be based on a number of factors, such as a desired or target flow rate, the volume of fluid to be infused, a desired or target infusion time, infusion fluid parameters such as fluid viscosity, temperature, and others. The fluid flow resistor 252 is rotated to the desired position by the output shaft 120 under programmed control via the gearbox 10 as detailed above. During the infusion, further adjustments may be made to the fluid flow resistor 252, for example, to fine tune flow rate in response to feedback provided by an inline flow sensor 262 or otherwise in accordance with the input infusion information. It will be recognized that valve position within the fluid flow resistor need not be the only means within the flow control system for controlling or adjusting flow rate, and that the flow resistor may be used in combination with other parameters, such as a fluid driving pressure in the pumping chambers 264, in order to achieve a desired flow rate.

In the depicted preferred embodiment, the administration set 250 may also include an inline flow sensor 262 for sensing flow rate. In the depicted embodiment, the flow sensor is integrally formed with the fluid flow resistor 252, although a separately formed flow rate sensor is also contemplated. The flow rate sensor 252 is preferably of a type that includes an moveable inline flow object or element (not shown), the position of which varies as a function of flow rate and the position of which can be monitored optically to determine an actual flow rate of the IV fluid as it passes out of the flow resistor 252 to the patient.

The flow object may be monitored, for example, by an optical sensor, which includes a light source 204 such as an LED array and an optical detector 206, which may be a photosensor array, such as a charged-coupled device (CCD) array or the like. The light source 204 and optical detector 206 are preferably disposed on opposite sides of a flow chamber containing the flow object, although other configurations are also contemplated, such as an optical detector 206 positioned to sense light emitted by the light source 204 and reflected by the flow object. The pattern of light is sensed by the detector 206 to determine the position of flow object within the flow resistor 252. The position information, in turn, is used to determine an actual fluid flow rate. The flow rate information can be sent to the electronic controller to provide feedback, which can in turn, be, used to control fluid flow in accordance with the infusion information.

The processing unit may also be programmed to shut off flow by rotating the resistor cap 254 to an off or closed position in response to a detected alarm condition, such as an occlusion, a detected an air bubble in the line, etc. In especially preferred embodiments, the fluid flow resistor 252 and/or inline flow rate sensor 262 may be as described in commonly owned International Patent Application No. PCT/US2009/068349 filed Dec. 17, 2009, entitled "Extended Range Fluid Flow Resistor," which is incorporated herein by reference in its entirety.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A gearbox, comprising:
an outer housing having a first side wall and a second side wall opposite and spaced apart from said first side wall;
an inner gear assembly received within said outer housing, said inner gear assembly comprising:
an inner housing;
a first gear member rotatably received within said inner housing; and
a second gear member having an output shaft rotatably supported on said inner housing and a toothed portion intermeshing with said first gear member;
a slider plate received within said outer housing and having a first plurality of axially aligned elongate openings and a second plurality of axially aligned elongate openings, said first plurality of elongate openings is aligned with a first axis and said second plurality of elongate openings is aligned with a second axis;
said first sidewall having a first plurality of pins, each one of said first plurality of pins running in a respective one of said first plurality of elongated openings to allow relative sliding movement between said outer housing and said slider plate along said first axis; and
said inner housing having a second plurality of pins, each one of said second plurality of pins running in a respective one of said second plurality of elongate openings to allow relative sliding movement between said inner housing and said slider plate along said second axis.

2. The gearbox of claim 1, wherein said output shaft has a first end and a second end opposite said first end, said toothed portion located between said first and second ends, and said first end extending through an opening in one of said second plurality of pins and through an opening in said first sidewall.

3. The gearbox of claim 2, wherein said second end extends through an opening in said inner housing and rotatably engages a rotary encoder for sensing a rotational position of said output shaft.

4. The gearbox of claim 3, further comprising:
an electric motor coupled to said first gear member; and
said rotary encoder controlling operation of said electric motor.

5. The gearbox of claim 1, wherein said first gear member is a worm and said second gear member is a worm wheel.

6. The gearbox of claim 5, wherein said second gear member is rotatable about a third axis.

7. The gearbox of claim 6, wherein said first axis, said second axis, and said third axis are mutually orthogonal.

8. The gearbox of claim 7, wherein each of said first and second axes intersects said third axis.

9. The gearbox of claim 7, wherein said second axis intersects said third axis and said first axis is displaced from said third axis.

10. The gearbox of claim 1, further comprising:
a tension member having a first end attached to said outer housing and a second end attached to said inner housing for urging said outer housing and said inner housing to a desired relative position.

11. The gearbox of claim 10, wherein said output shaft is removably attached to a driven member, said inner gear assembly movable against the urging of said tension member to accommodate misalignment between said output shaft and said driven member.

12. The gearbox of claim 1, further comprising:
an electric motor coupled to said first gear member for rotating said first gear member.

13. A fluid flow control system for use in administering an IV fluid to a subject, the fluid flow control system including a pump assembly having a gearbox mounted therein for rotatably adjusting a rotatably adjustable flow resistor, the gearbox comprising:
an outer housing having a first side wall and a second side wall opposite and spaced apart from said first side wall;
an inner gear assembly received within said outer housing, said inner gear assembly comprising:
an inner housing;
a first gear member rotatably received within said inner housing; and
a second gear member having an output shaft rotatably supported on said inner housing, a toothed portion intermeshing with said first gear member, and said output shaft coupled to said second gear member;
a slider plate received within said outer housing and having a first plurality of axially aligned elongate openings and a second plurality of axially aligned elongate openings, wherein said first plurality of elongate openings is aligned with a first axis and said second plurality of elongate openings is aligned with a second axis;
said first sidewall having a first plurality of pins, each one of said first plurality of pins running in a respective one of said first plurality of elongated openings to allow relative sliding movement between said outer housing and said slider plate along said first axis; and
said inner housing having a second plurality of pins, each one of said plurality of pins running in a respective one of said second plurality of elongate openings to allow relative sliding movement between said inner housing and said slider plate along said second axis.

* * * * *